US006327368B1

(12) United States Patent
Yamaguchi et al.

(10) Patent No.: US 6,327,368 B1

(45) Date of Patent: Dec. 4, 2001

(54) CONFIGURATION OF PROVIDING MICROPHONE IN DUCT AND ACTIVE NOISE REDUCTION DEVICE USING SAME

(75) Inventors: Atsushi Yamaguchi; Hiroyuki Furuya, both of Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1108 days.

(21) Appl. No.: 08/779,024

(22) Filed: Jan. 6, 1997

Related U.S. Application Data

(63) Continuation of application No. 08/300,079, filed on Sep. 2, 1994, now abandoned.

(30) Foreign Application Priority Data

Dec. 10, 1993 (JP) .................................................. 5-341608

(51) Int. Cl.$^7$ .......................... A61F 11/06; G10K 11/16; H03B 29/00

(52) U.S. Cl. ........................ 381/71.5; 381/71.7; 381/365; 181/224

(58) Field of Search .............................. 381/71, 94, 73.1, 381/168–9, 189, 71.1–71.14, 355, 361, 365; 415/119; 181/224, 227, 206, 291

(56) References Cited

U.S. PATENT DOCUMENTS

| | | | | |
|---|---|---|---|---|
| 4,527,282 | * | 7/1985 | Chaplin et al. | 381/94 |
| 4,749,150 | * | 6/1988 | Rose et al. | 181/214 |
| 4,989,688 | * | 2/1991 | Nelson | 181/291 |
| 5,278,780 | * | 1/1994 | Eguchi | 381/71.5 |

FOREIGN PATENT DOCUMENTS

| | | | | |
|---|---|---|---|---|
| 3188798 | * | 8/1991 | (JP) | 381/71 |

* cited by examiner

*Primary Examiner*—Xu Mei
(74) *Attorney, Agent, or Firm*—Staas & Halsey LLP

(57) ABSTRACT

A configuration of providing a microphone in a duct having an air current therein, for use in an active noise reduction device for reducing noise propagating in the duct by producing sounds counteracting the noise, includes an expanded room formed by enlarging an area of a cross section of part of the duct, wherein the cross section is perpendicular to a direction of the air current, and a microphone provided in the expanded room for picking up the noise in order to produce signals for the sounds.

8 Claims, 9 Drawing Sheets

CONFIGURATION OF PROVIDING MICROPHONE IN DUCT AND ACTIVE NOISE REDUCTION DEVICE USING SAME

This application is a continuation of application Ser. No. 08/300,079, filed Sep. 2, 1994, now abandoned.

BACKGROUND OF THE INVENTION

1. Field of the Invention

The present invention relates to a configuration in which a microphone is attached inside a duct, for use in an active noise reduction device employing an active noise control technique for reducing a noise generated by information processing equipment and the like.

Information processing equipment and the like include ventilating of the inside of the equipment in order to release heat generated inside the equipment to the outside. In recent years, there has been a demand for better office environments with information processing equipment with lower noise levels, so that noise coming out of such equipment need to be reduced. However, noise reduction measures taken for each device component is not enough to achieve this end, and sound absorbing ducts with acoustical material affixed therein are used in exit openings of ventilators. In addition to that, in order to eliminate a noise which is not erased by sound absorbing ducts, an active noise control technique is used for counteracting this noise by using a sound of the same magnitude and a reversed phase.

2. Description of the Prior Art

As shown in FIG. 1, a typical mechanism for releasing inside heat to the outside has duct 2 provided with a fan 1, which generates a current of air for releasing inside heat. One of the methods of reducing noise inside the duct 2 is to paste inside the duct 2 acoustic material 3 such as forming material. This method is mainly concerned with a reduction of high pitched sounds in noise.

As noted above, the acoustic material 3 mainly absorbs high frequency components of noise, and is not suitable for the reduction of low frequency components. An active noise control method is a method of reducing such noise persisting despite the acoustic material 3.

FIG. 2 shows an example of a prior art control system for an active noise reduction device employing the active noise control method. As shown in FIG. 2, the active noise reduction device comprises a noise reduction filter 10, a reversing sound compensation filter 11, a FIR (Finite Impulse Response) filter 12, an arithmetic operation control unit 13, a speaker 14, a noise pick-up microphone 4, and an error pick-up microphone 15.

The noise pick-up microphone 4 is a microphone which is provided on the side of a noise source to pick up noise. The noise reduction filter 10 is a FIR filter which generates a noise reduction signal by using as a reference signal a noise signal picked up by the microphone 4, and which emulates a transfer system A of the noise.

The speaker 14 is used for transforming the noise reduction signal produced by the noise reduction filter 10 into a noise reduction sound, and superimposes this sound on noise coming through the transfer system A of the duct. The error pick-up microphone 15 is a microphone which picks up persisting noise (difference between noise and the noise reduction sound) in order to update filter coefficients of the noise reduction filter 10. A signal detected by the microphone 15 is provided for the arithmetic operation control unit 13.

The FIR filter 12 is a filter for emulating a transfer system B which is constituted by the path from the output of the noise reduction filter 10 to the error signal input of the noise reduction filter 10 via the speaker 14 and the error pick-up microphone 15. The FIR filter 12 is provided in order to factor in the influence of the transfer system B by using such algorithms as Filtered-x, because noise to be reduced cannot be counteracted in the noise reduction device unless the output of the noise reduction filter 10 passes through the transfer system B including the speaker 14.

The arithmetic control unit 13 is a circuit which controls the noise reduction filter 10 by executing arithmetic operations used for updating its filter coefficients on the basis of the output of the FIR filter 12 and a signal picked up by the microphone 15.

The reversing sound compensation filter 11 is a filter which emulates a transfer system C directing upstream in the same path as the transfer system A. In the noise reduction device, the noise reduction sound transmitted by the speaker 14 propagates in the transfer system C directing upstream in the same path as the transfer system A to reach the noise pick-up microphone 4, which obstructs the generation of a proper noise reduction sound by the noise reduction filter 10. In order to negate the effect of this reversing sound which passes through the transfer system C, the noise reduction device emulates the transfer system C to produce a reversing sound signal by passing the noise reduction signal of the noise reduction filter 10 through the reversing sound compensation filter 11, and subtracts this reversing sound signal from the signal picked up by the noise reduction microphone 4.

When employing active noise control, a proper noise control cannot be implemented if a microphone provided in a duct picks up noise generated by a current of air therein. This noise is sounds made by a friction of air with the microphone and, also, made by shaking movement of the microphone blown by an air current. Thus, a proper counter measure for the air current becomes necessary. A counter measure for the air current in the prior art is to plant a microphone in the acoustic material pasted on the inside wall of the duct, thus reducing an effect of the air current on the microphone.

However, keeping pace with recent development of information processing equipment, heat generated inside the equipment has a tendency to increase. Thus, there is a need to increase a heat release capacity of the equipment, which leads to the use of fans having a larger capacity of ventilating. As a result, the velocity of a current passing through a duct becomes higher, which means that an effect of the current on a microphone provided in the duct is also increased. Accordingly, it becomes necessary to develop more advanced technologies for air current counter measures.

Accordingly, there is a need in the fields of active noise reduction devices for a configuration of providing a microphone in a duct which can reduce an effect of an air current on the microphone, and realize a higher noise reduction capacity.

SUMMARY OF THE INVENTION

Accordingly, it is a general object of the present invention to provide for an active noise reduction device a configuration of providing a microphone in a duct which can satisfy the need described above.

It is another and more specific object of the present invention to provide an active noise reduction device having a microphone in a duct which can reduce an air current on the microphone, and realizing a higher noise reduction capacity.

In order to achieve the above objects, according to the present invention, a configuration of providing a microphone in a duct having an air current therein, for use in an active noise reduction device for reducing noise propagating in the duct by producing sounds counteracting the noise, includes an expanded room formed by enlarging an area of a cross section of part of the duct, wherein the cross section is perpendicular to a direction of the air current, and a microphone provided in the expanded room for picking up the noise in order to produce signals for the noted sounds.

With this configuration, the air current running through the duct reduces its velocity when it comes to the expanded room, since the area of the cross section is enlarged therein. Thus, an effect of the air current on the microphone can be reduced, and an active noise reduction device employing this configuration can effectively eliminate noise inside the duct by producing an appropriate counteracting sound.

Other objects and further features of the present invention will be apparent from the following detailed description when read in conjunction with the accompanying drawings.

DESCRIPTION OF THE PREFERRED EMBODIMENTS

First, a description will be given of a principle of the present invention with reference to FIG. 3.

Figure 3:
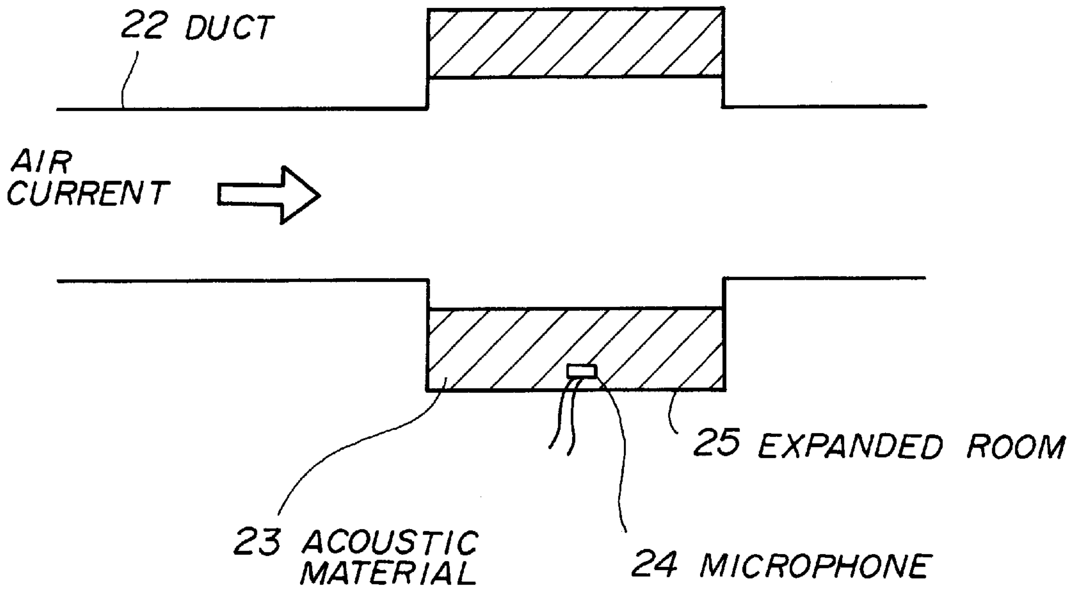
FIG. 3 is an illustrative drawing showing a principle of the present invention.

FIG. 3 shows a principle of the present invention.

The configuration of providing a microphone in a duct according to the principle of the present invention is used in a mechanism in which a microphone 24 detects sound propagating inside the duct 22 with an air current running through. This configuration, as an exemplary one, has an expanded room 25 which is made in some length of the duct 22 by extending the area of a cross section thereof perpendicular to the direction of an air current, and provides a microphone 24 inside the expanded room 25.

An air current running through the duct decreases its velocity when it comes to the expanded room, as the area of a cross section perpendicular to the direction of the air current becomes larger. Thus, an effect of the air current on the microphone can be reduced. Also, as the expanded room itself has a function of a silencer, a noise reduction effect can be obtained.

Another configuration of providing a microphone in a duct according to the principle of the present invention has the microphone 24 planted in an acoustic material 23 which is affixed to the inside wall of the expanded room 25.

Providing an acoustic material 23 inside the expanded room 25 can bring about a reduction of high frequency component in noise. Also, preventing the microphone 24 from having a direct exposure to the air current can reduce an effect of the air current on the microphone 24.

Yet another configuration of providing a microphone in a duct according to the principle of the present invention has an expanded room 25 of a streamlined shape with a gradual increase and a gradual decrease in a size of the cross section in a direction of the air current.

Streamlining a shape of the expanded room 25 can make the flow of the air current smooth, and thereby an effect of the air current on the microphone 24 can be reduced.

Still another configuration of providing a microphone in a duct according to the principle of the present invention uses as an expanded room 25 an elbow of the duct as it is, or forms an expanded room at an elbow of the duct.

The use of the configurations described above in an active noise reduction device employing an active noise control can enhance the performance of the active noise reduction device.

In the following, embodiments of the present invention will be described with reference to the accompanying drawings. In the following drawings, elements which have identical functions will be referred to by the same numerals.

Figure 1:
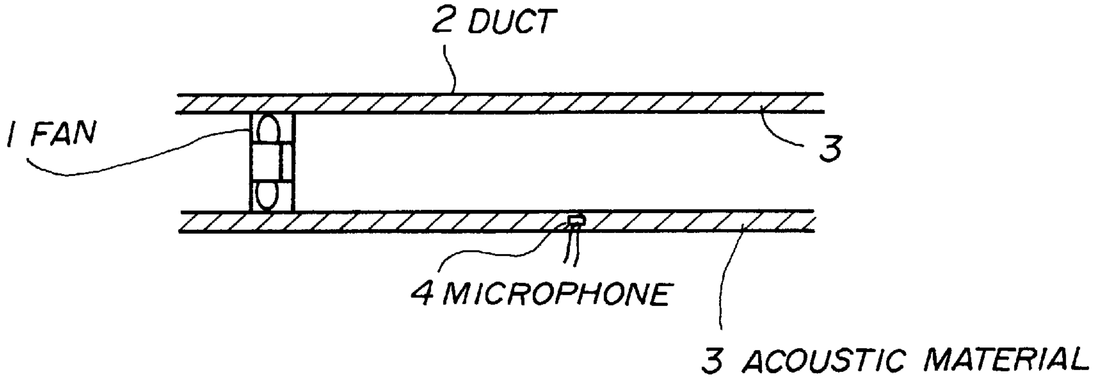
FIG. 1 PRIOR ART
FIG. 1 is an illustrative drawing showing a configuration of providing a microphone in a duct of the prior art.
Figure 2:
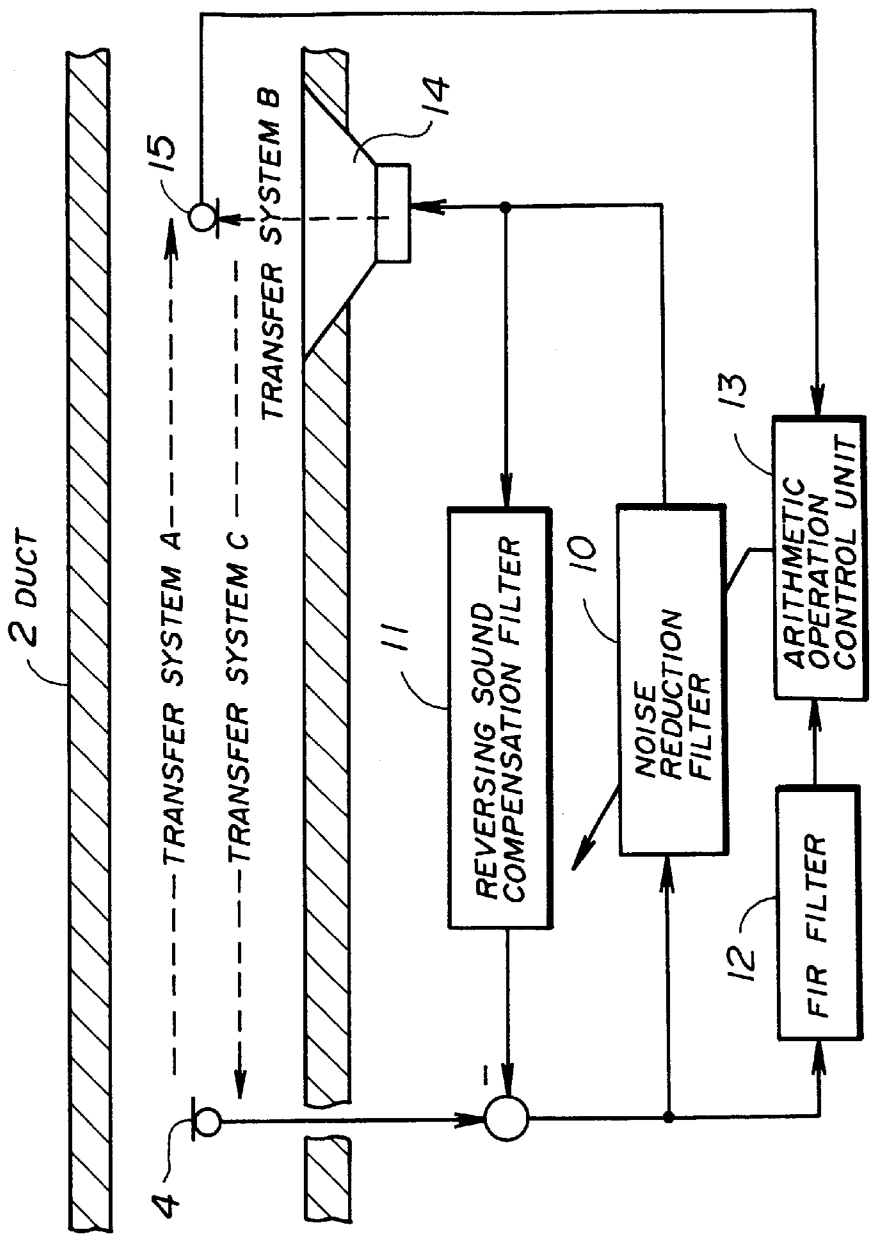
FIG. 2 PRIOR ART
FIG. 2 is a block diagram of an active noise reduction device of the prior art.

It may be noted that the following embodiments of configurations of providing a microphone in a duct according to the present invention are used for an active noise reduction device as shown in FIG. 2. That is, various configurations disclosed below of providing a microphone in a duct are designed to be used in an active noise reduction device in order to reduce an effect of an air current on a microphone as well as noise themselves inside the duct.

Figure 4A:
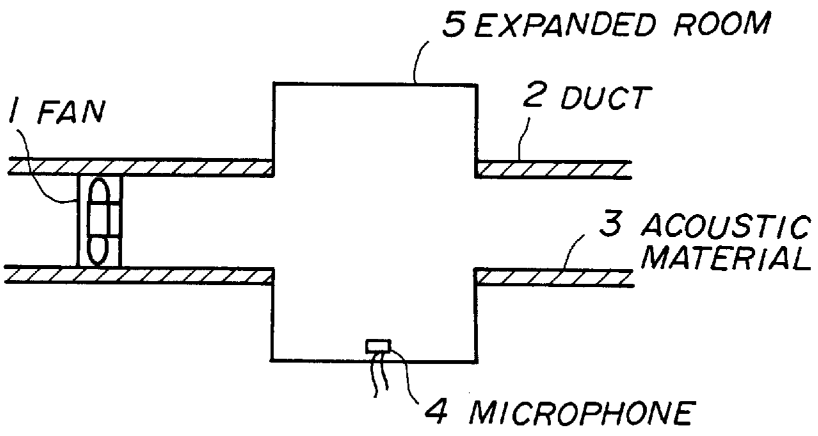
FIGS. 4A to 4C are illustrative drawings showing configurations of providing a microphone in a duct according to a first embodiment of the present invention.
Figure 4B:
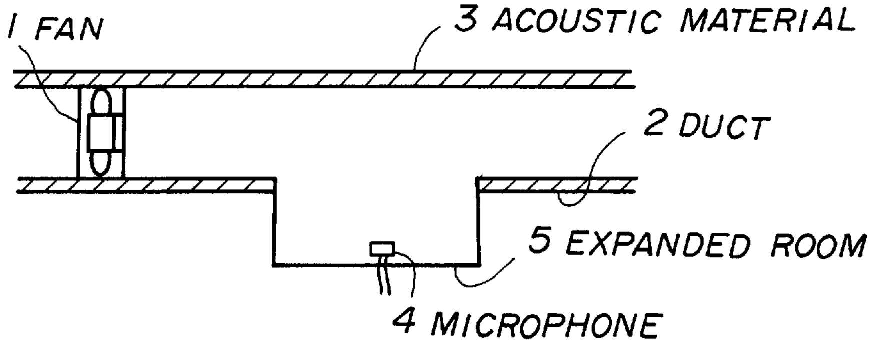
Figure 4C:
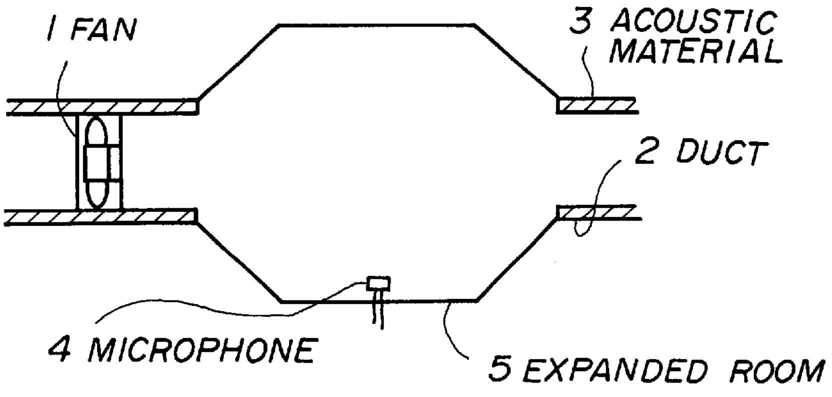

FIGS. 4A, 4B, and 4C show configurations of providing a microphone in a duct according to a first embodiment of the present invention. In FIG. 4A, a duct 2 is provided with a fan 1 for generating an air current for ventilating, and an expanded room 5 is formed downstream in part of the duct 2 by extending an area of a cross section of duct 2, which cross section is perpendicular to the direction of the air current. A noise pick-up microphone 4 of an active noise reduction device is mounted in the expanded room 5. Acoustic material 3 of foaming material is affixed to the inside wall of the duct 2 except that of the expanded room 5.

With such a configuration of providing a microphone in a duct, an air current provided by the fan 1 into the duct 2 decreases its velocity when reaching the expanded room 5, since the cross sectional area thereof is larger than other parts. Thus, the amount of the air current blowing on the microphone 4 can be reduced, and, thus, an effect of the air current on the microphone can also be reduced.

By providing the expanded room 5 in the path of noise propagation, the expanded room 5 itself serves as a conventional silencer of an expansion type, and has noise reduction characteristics defined by an expansion ratio of a cross section. Thus, compared to a configuration of the prior art without an expansion room, this configuration has an effect to reduce noise propagating inside the duct.

As described above, the configuration shown in FIG. 4A can reduce an effect of the air current, and provide a noise reduction effect by serving as an expansion type silencer.

Various shapes can be used for the expanded room 5, so that, for example, the expanded room 5 can be a cylindrical shape or a box shape. Or the expanded room 5 can be provided only on one side of the duct 2, as shown in FIG. 4B. Also, as will be described below, an elbow of a duct can be used as an expanded room by taking advantage of the fact that a cross sectional area extends in effect at the elbow of the duct. Of course, an expanded room may be provided at the elbow of the duct.

Furthermore, as shown in FIG. 4C, a configuration can be such that a cross sectional area is made extending gradually as it goes downstream on the side of the entrance of the expanded room 5, while contracting gradually as it goes downstream on the side of the exit of the expanded room 5. Or the expanded room 5 can be streamlined. With such configurations, the air current entering the expanded room can flow smoothly without disturbance, so that a harmful effect of the air current on the microphone can be reduced. As a result, a noise reduction effect of the active noise reduction device can be enhanced.

Figure 5A:
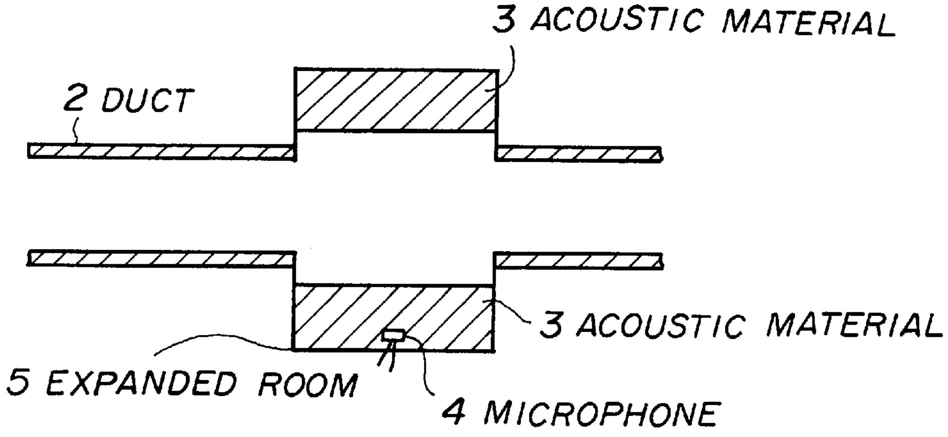
FIGS. 5A to 5C are illustrative drawings showing configurations of providing a microphone in a duct according to a second embodiment of the present invention.
Figure 5B:
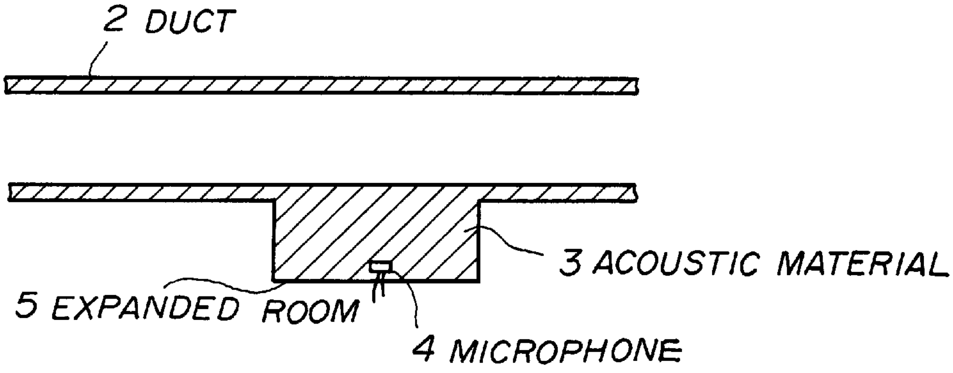
Figure 5C:
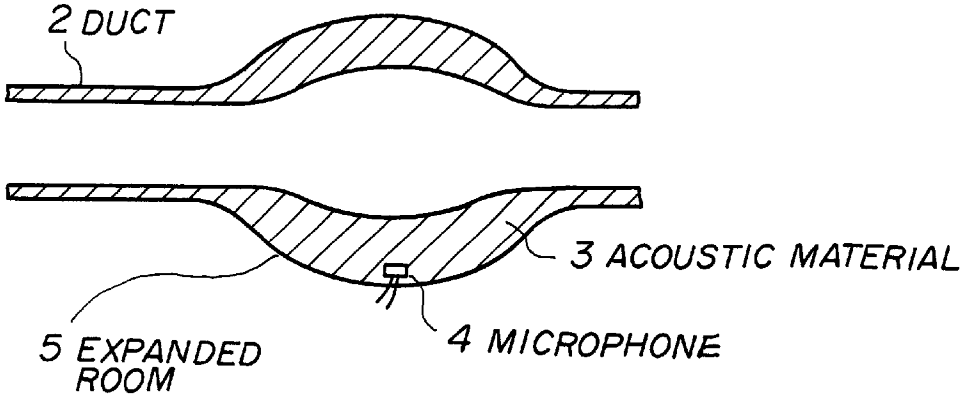

FIGS. 5A, 5B, and 5C show a second embodiment of the present invention. In this embodiment, the acoustic material 3 of forming material is affixed also to the inside wall of the expanded room 5, and the microphone 4 is planted in the acoustic material 3. Since noise frequencies which an active noise reduction device concerns is relatively low, high frequency components will persist. The acoustic material 3 made of forming material generally has a nature to absorb sound of high frequencies, so that the acoustic material 3 can absorb the persisting noise noted above.

In FIG. 5A, the acoustic material 3 affixed to the inside of the expanded room 5 is made thicker than that of other parts of the duct 2. Thus, an effect of the air current on the microphone 4 can be reduced compared to the case of the prior art by the amount contributed by both the expansion of a cross sectional area in the expanded room 5 and the thickness of the acoustic material 3. Even though the expanded room 5 is filled in part with the acoustic material 3, a function of the expanded room 5 as an expansion silencer is not lost by the acoustic material 3. Thus, a noise reduction effect can be obtained in this case as well.

In FIG. 5B, the expansion room 5 is fully filled with the acoustic material 3. In this case, a cross sectional area for an air current to go through is in effect the same as that of the other parts of the duct 2, so that the velocity of the air current is the same as that of a conventional configuration. However, an effect of the air current on the microphone 4 can still be reduced by the amount corresponding to the additional thickness of the acoustic material 3. Also, a function of the expanded room 5 as an expansion silencer is not lost by the acoustic material 3. Thus, a noise reduction effect of an expansion silencer is obtained as well.

In FIG. 5C, the expanded room 5 is made streamlined, and, also, the acoustic material 3 affixed to the inside of the expanded room 5 is made streamlined inside. With this configuration, the flow of the air current becomes smooth so that a harmful effect of air current disturbance on the microphone can be reduced.

Comparisons of the above variations of first and second embodiments with each other may be better to be summarized here with regard to various effects, i.e., a silencer effect, an acoustic material sound absorbing effect, and an effect of reducing influences from the air current.

The first two effects listed above concern a reduction of noise on their own. On the other hand, the last one, i.e., an effect of reducing influences from an air current concerns an effectiveness of an active noise reduction device. So, the first two effects and the last effect are best examined separately.

With or without the existence of acoustic material, a silencer effect does not change. Also, acoustic material has a noise reduction effect on high frequency components of noise as noted above, which contrasts with a reduction in low frequency components by a silencer effect as well as an active noise control. Actually, acoustic material in general is effective in reducing noise of frequencies higher than 2 kHz. In one embodiment, which has an expansion room of an approximately 20 cm×20 cm box shape and a duct of an approximately 5 cm diameter, a silencer effect can be seen in frequencies less than 1 kHz. Also, in general, an active noise reduction is effective for frequencies less than 2 kHz.

Accordingly, the second embodiment, which has acoustic material provided inside an expanded room, is better than the first embodiment in consideration of noise reduction effects themselves.

On the contrary, the velocity of an air current running through an expanded room is lower for the first embodiment as it has in effect a larger area of a cross section. However, acoustic material provided for the second embodiment prevents a direct exposure of a microphone to an air current. Thus, in total, an effect of an air current on a microphone does not have a significant difference between the first embodiment and the second embodiment.

Accordingly, in consideration of all the three effects cited above, it can be expected that variations of the second embodiment have better result of reducing noise than do those of the first embodiment.

Figure 6A:
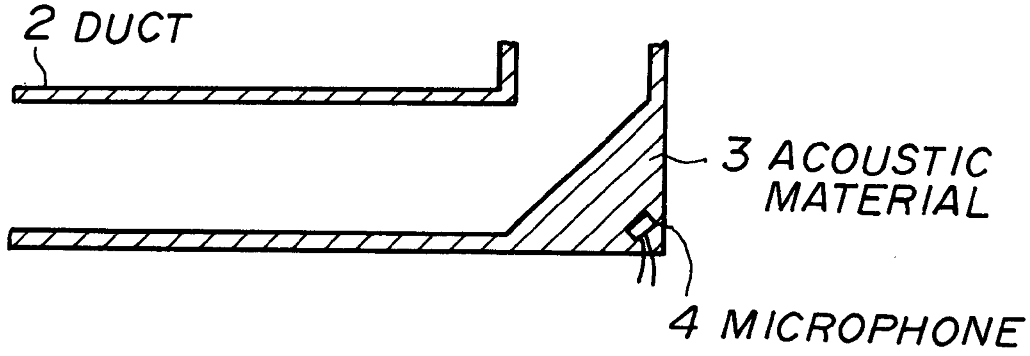
FIGS. 6A and 6B are illustrative drawings showing configurations of providing a microphone in a duct according to a third embodiment of the present invention.
Figure 6B:
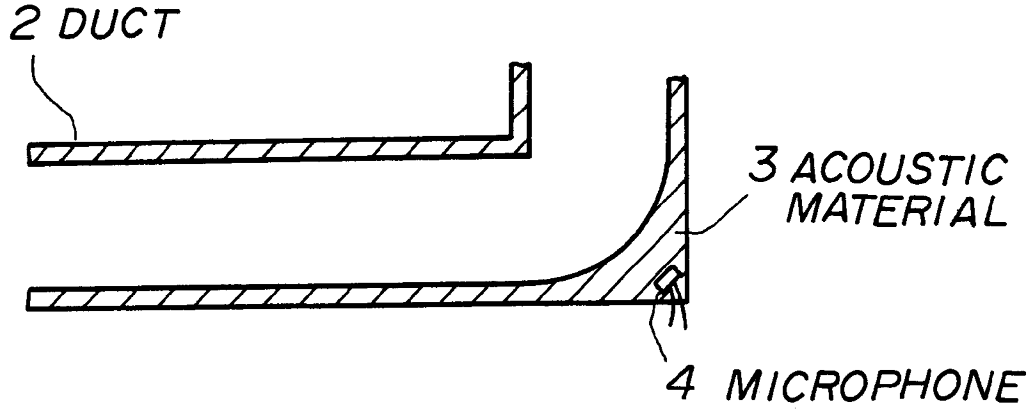

FIGS. 6A and 6B show a third embodiment of the present invention. In this embodiment, an elbow of the duct 2 is used as an expanded room by utilizing the fact that an area of a cross section perpendicular to the direction of the air current is extended at an elbow of the duct 2. In this configuration, the acoustic material 3 is made thicker at the outside corner of the elbow, and the microphone 4 is planted therein.

In FIG. 6A, the acoustic material 3 has a shape of a triangle at a cross section parallel to the surface of FIG. 6A. When the acoustic material 3 is affixed in this manner, a cross sectional area is the same as that of other parts of the duct. But an effect of the air current on the microphone is reduced by the amount corresponding to the thickness of the acoustic material 3.

In FIG. 6B, the acoustic material 3 has a rounded surface. With this surface shape of the acoustic material 3, the flow of the air current running through that part is made smooth so that an effect of air current disturbance on the microphone can be decreased.

Figure 7A:
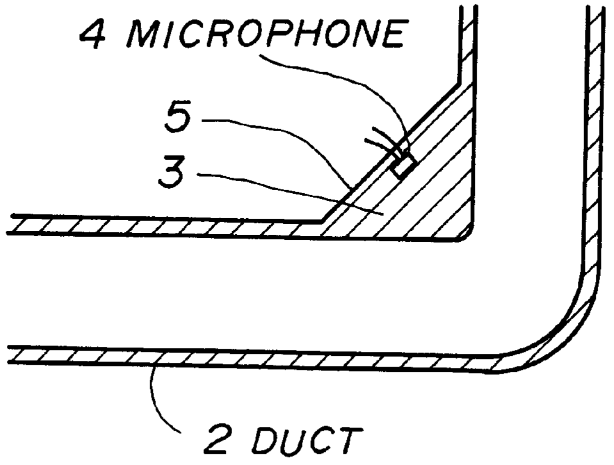
FIGS. 7A and 7B are illustrative drawings showing configurations of providing a microphone in a duct according to a fourth embodiment of the present invention.
Figure 7B:
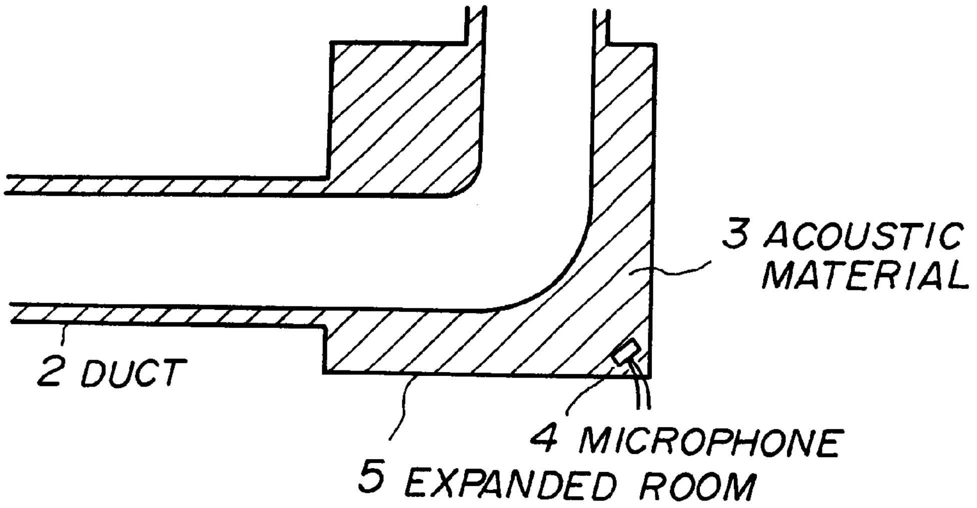

FIGS. 7A and 7B show a fourth embodiment of the present invention. This embodiment does not use an elbow of the duct 2 as an expanded room as it is, but forms an expanded room 5 at and in addition to the elbow.

In FIG. 7A, the inside corner of an elbow of the duct 2 is dented inwards, and this enlarged part is filled with the acoustic material 3 having a shape of a triangle in a cross section parallel to the surface of FIG. 7A. The microphone 4 is planted in the acoustic material 3, while the outside corner of the elbow is made round.

In FIG. 7B, the expanded room 5 of a box shape is formed at the elbow of the duct 2. The acoustic material 3 is filled in the expanded room 5 so as to form an air current path which has a cross sectional area for the air current to run through the same size as the other part of the duct 2. The microphone 4 is planted in the acoustic material 3 at the outside corner.

In both FIG. 7A and FIG. 7B, the cross sectional area for the air current to run through is the same as that of the other part of the duct 2. Since the acoustic material 3 is made thicker than that of the third embodiment, however, an effect of the air current on the microphone can be reduced accordingly. Also, the expanded room 5 itself which serves as an expansion silencer has a noise reduction effect.

Figure 8:
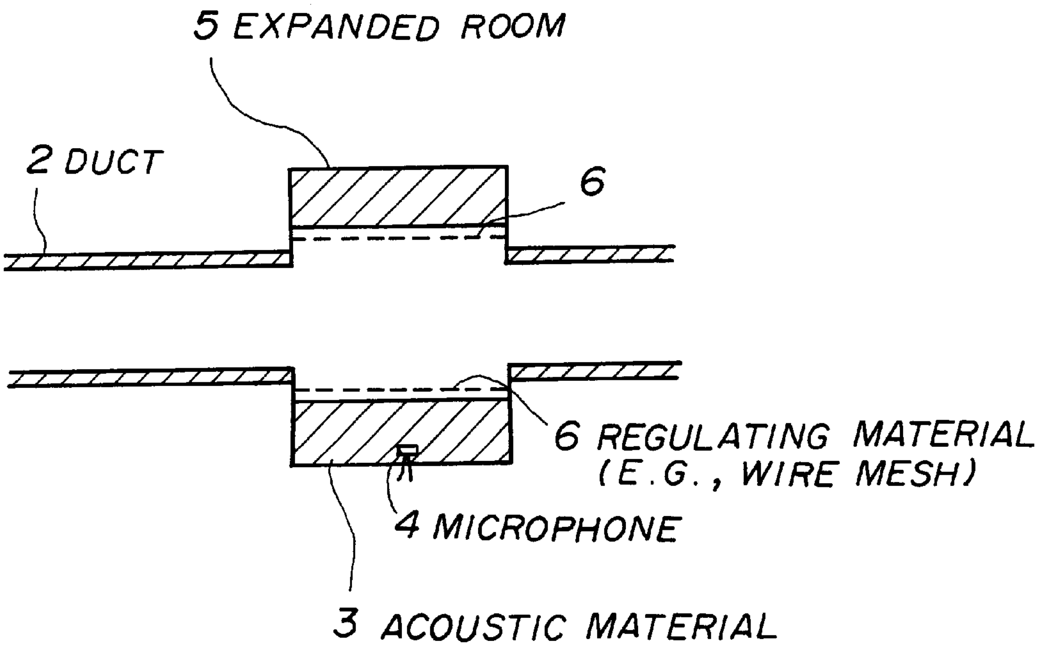
FIG. 8 is an illustrative drawing showing a configuration of providing a microphone in a duct according to a fifth embodiment of the present invention.

In FIG. 8, a fifth embodiment of the present invention is shown. A configuration of this embodiment is provided with an air regulating element 6 made of wire mesh or fabric for regulating the flow of the air current, as an additional component to the configuration of FIG. 5A. As the air current runs through wire mesh and the like, an effect of the air current on the microphone 4 can be reduced.

However, the effectiveness of wire mesh or fabric as a means for reducing a bad effect of an air current on a microphone is limited to the case where the velocity of an air current is not so high. This is because an air current running through wire mesh or fabric makes a sound through friction with the wire mesh or fabric. Also, the wire mesh or fabric itself makes a sound by vibrating when an air current runs through it. Thus, only when the velocity of an air current is less than 10 m/sec more or less, can their effectiveness for reducing an effect of an air current on a microphone be observed.

In the embodiments described above, the microphone mounted inside the expanded room is assumed to be a noise pick-up microphone of an active noise reduction device. However, it is apparent that the present invention is not limited to an application for a noise pick-up microphone, and a configuration of the present invention can be applied to an error pick-up microphone of an active noise reduction device.

Figure 9:
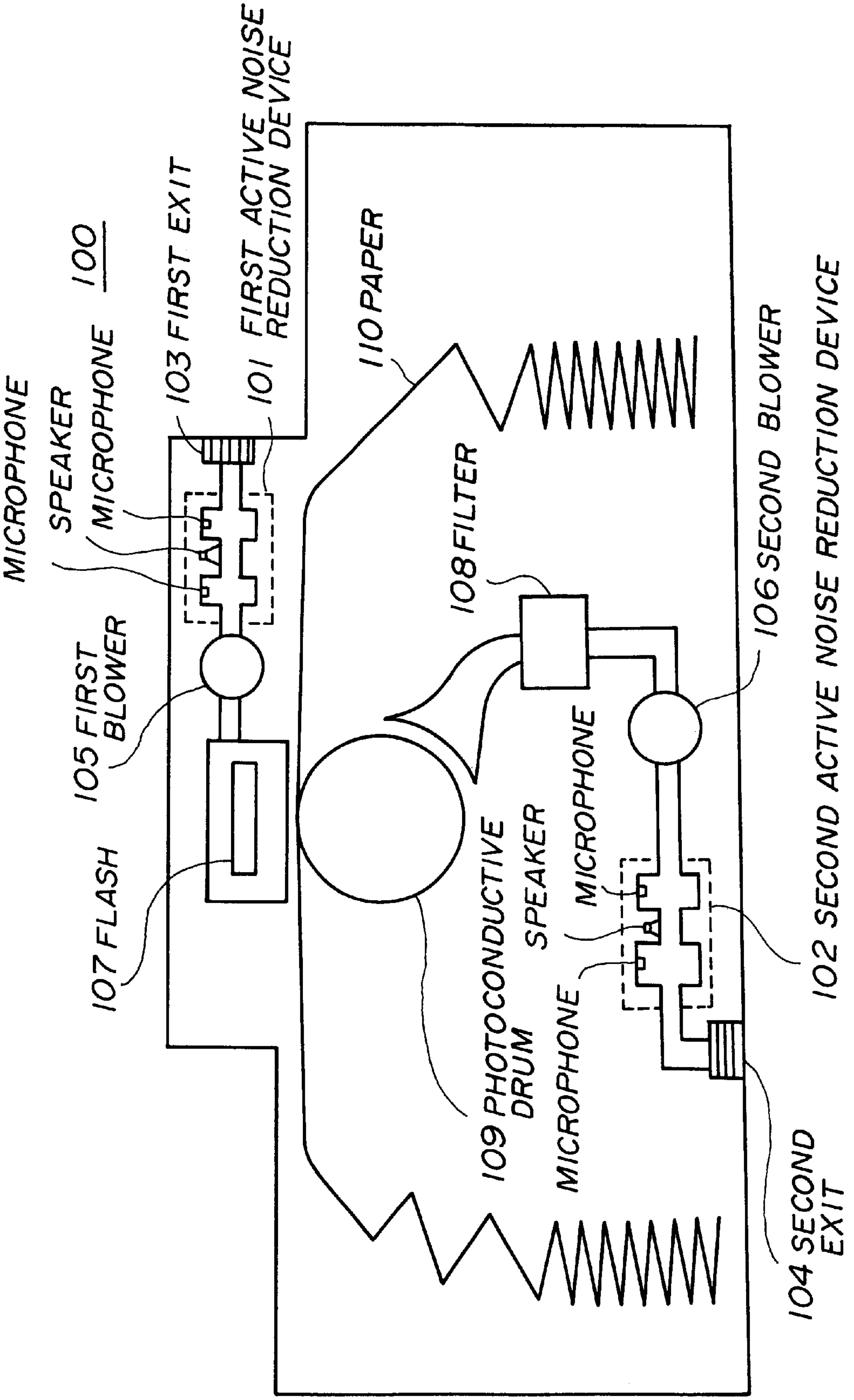
FIG. 9 is an illustrative drawing showing a printer device using an active noise reduction device with a configuration of providing a microphone in a duct according to the present invention.

FIG. 9 shows a sixth embodiment of the present invention, where active noise reduction devices having a configuration according to the present invention are used in a printer device.

In FIG. 9, the printer device 100 comprises a first active noise reduction device 101, a second active noise reduction device 102, a first exit 103, a second exit 105, a first blower 104, a second blower 106, a flash 107, a filter 108, a photoconductive drum 109, and paper 110.

Toner is made attached on the surface of the photoconductive drum 109, and, then, exposed to heat of the flash 107 to be printed on the paper 100. Surplus toner is sucked to be collected into the filter 108 by an air current made by the second blower 106. This air current runs through the second active noise reduction device 102 to be discharged from the second exit 104. Heat generated by the flash 107 is released from the first exit 103 by the first blower 105, whose noise is reduced by the first active noise reduction device 101.

As in FIG. 9, an active noise reduction device according to the present invention can be used for vacuum cleaning as well as releasing heat. Also, as can be seen in FIG. 9, a configuration in which a microphone is provided in an expanded room of a duct can be used for both a pick-up microphone and an error pick-up microphone by providing two expanded rooms.

As described above, according to the present invention, an effect of an air current which a microphone in a duct is subject to can be reduced, so that an active noise control can be effective with a reduced influence of the air current even in a strong air current for enhancing a heat release capacity. Also, the expanded room itself can have a noise reduction effect by serving as a silencer of an expansion type. This can supplement a noise reduction capacity of an active noise reduction device, contributing to the enhancement of product quality of the device.

Further, the present invention is not limited to these embodiments, but various variations and modifications may be made without departing from the scope of the present invention.

What is claimed is:

1. A configuration of providing a microphone in a duct having an air current therein, for use in an active noise reduction device having said microphone pick up noise propagating in said duct, having a speaker producing sounds counteracting said noise, and having an auxiliary microphone provided downstream from said microphone for picking up remnant noise, said speaker and said auxiliary microphone forming a closed loop for suppressing said remnant noise, said configuration comprising:

an expanded room formed by enlarging an area of a cross section of part of said duct, said cross section being perpendicular to a direction of the air current, the air current having a decrease in velocity when coming into said expanded room, wherein said microphone, provided upstream from said auxiliary microphone and farther from said speaker than said auxiliary microphone, is contained in said expanded room for picking up said noise, the decrease in velocity of the air current reducing an effect of the air current on said microphone in picking up said noise.

2. The configuration as claimed in claim 1, wherein said expanded room is streamlined having a gradual increase and a gradual decrease in a size of the cross section with respect a direction of said air current.

3. The configuration as claimed in claim 1, wherein said expanded room is streamlined having a gradual increase and a gradual decrease in a size of the cross section in a direction of said air current.

4. The configuration as claimed in claim 1, wherein said expanded room is an elbow of said duct.

5. The configuration as claimed in claim 1, wherein said expanded room is formed at an elbow of said duct.

6. The configuration as claimed in claim 1, further comprising an air regulating material provided on the surface of said acoustic material.

7. An active noise reduction device for reducing noise propagating inside a duct having an air current therein, by producing sounds counteracting said noise, said active noise reduction device comprising:

an expanded room formed by enlarging an area of a cross section of part of said duct, said cross section being perpendicular to a direction of the air current, the air current having a decrease in velocity when coming into said expanded room;

a microphone provided in said expanded room for picking up said noise to produce noise signals representing said noise, the decrease in velocity of the air current reducing an effect of the air current on said microphone in picking up said noise;

emulating means for producing sound signals by using said noise signals by emulating a transfer system of said duct with regard to said noise propagating therein;

speaker means for producing said sounds by using said sound signals in order to counteract said noise; and an auxiliary microphones provided downstream from said microphone and nearer to said speaker means than said microphone, for picking up remnant noise, said auxiliary microphone and said speaker means forming a closed loop for suppressing said remnant noise.

8. A device which needs to send out air from the inside of said device while reducing noise generated in sending out said air, said device comprising:

a duct for sending out said air;

blower means for generating an air current in said duct in order to send out said air; and an active noise reduction device for reducing said noise propagating inside said duct by producing sounds counteracting said noise, said device including:

an expanded room formed by enlarging an area of a cross section of part of said duct, said cross section being perpendicular to a direction of the air current, the air current having a decrease in velocity when coming into said expanded room;

a microphone provided in said expanded room for picking up said noise to produce noise signals representing said noise, the decrease in velocity of the air current reducing an effect of the air current on said microphone in picking up said noise;

emulating means for producing sound signals by using said noise signals by emulating a transfer system of said duct with regard to the said noise propagating therein;

speaker means for producing said sounds by using said sound signals in order to counteract said noise; and an auxiliary microphone, provided downstream from said microphone and nearer to said speaker means than said microphone, for picking up remnant noise, said auxiliary microphone and said speaker means forming a closed loop for suppressing said remnant noise.

* * * * *

UNITED STATES PATENT AND TRADEMARK OFFICE
CERTIFICATE OF CORRECTION

PATENT NO. : 6,327,368 B1
DATED : December 4, 2001
INVENTOR(S) : Atsuhi Yamaguchi It is certified that error appears in the above-identified patent and that said Letters Patent is hereby corrected as shown below:

Column 9,
Line 3, change "microphones" to -- microphone, --.

Signed and Sealed this

Third Day of December, 2002

JAMES E. ROGAN
*Director of the United States Patent and Trademark Office*